Figure 1:
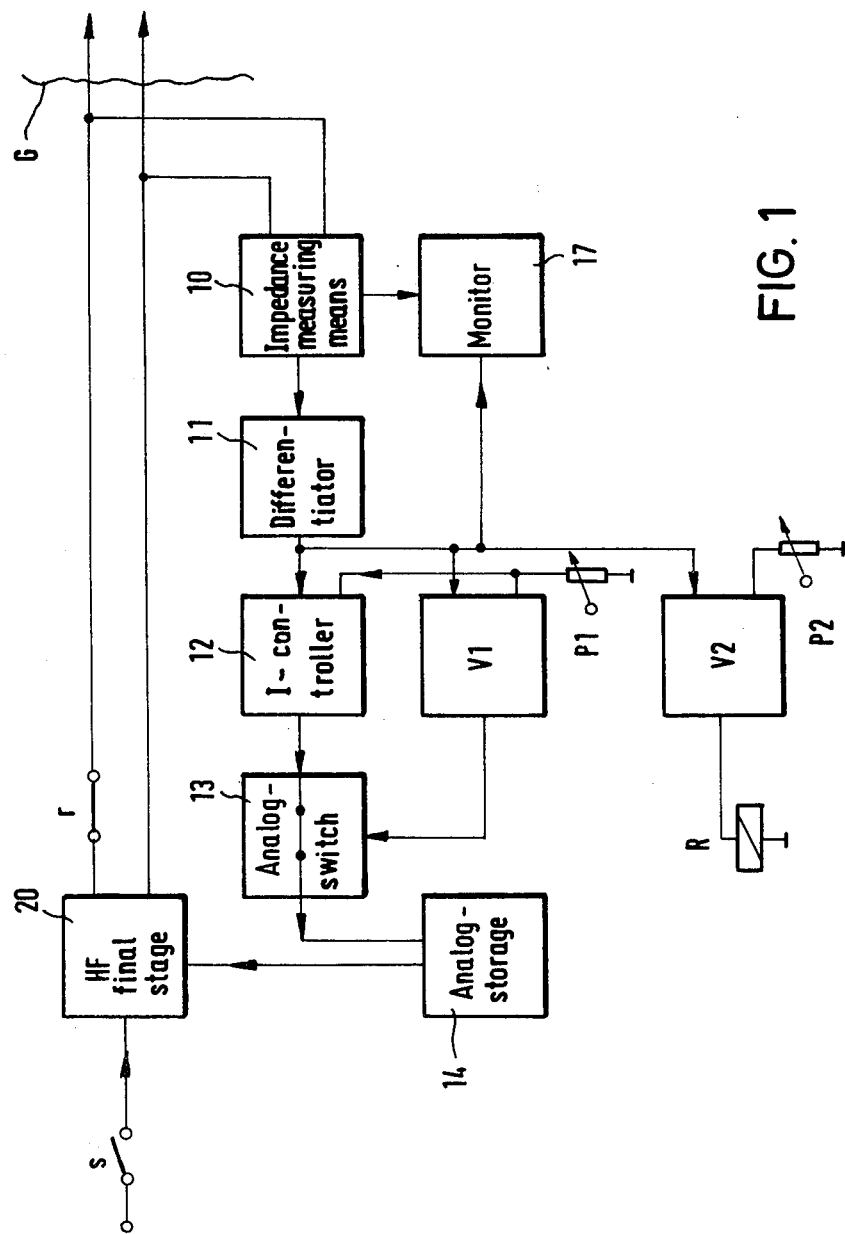

United States Patent [19]

Koch

[11] Patent Number: 4,474,179

[45] Date of Patent: Oct. 2, 1984

[54] METHOD AND APPARATUS FOR THE HIGH FREQUENCY COAGULATION OF PROTEIN FOR SURGICAL PURPOSES

[75] Inventor: Rainer Koch, Mengen, Fed. Rep. of Germany

[73] Assignee: F. L. Fischer GmbH & Co., Freiburg, Fed. Rep. of Germany

[21] Appl. No.: 377,932

[22] Filed: May 13, 1982

[30] Foreign Application Priority Data

May 20, 1981 [DE] Fed. Rep. of Germany ....... 3120102

[51] Int. Cl.³ ............................................. A61B 17/39
[52] U.S. Cl. ................................................ 128/303.17
[58] Field of Search ........................ 128/303.13–303.18

[56] References Cited

U.S. PATENT DOCUMENTS 4,321,926  3/1952  Roge ................................. 128/303.18
4,372,315  2/1983  Shapiro et al. .................. 128/303.18

FOREIGN PATENT DOCUMENTS 2455171  8/1976  Fed. Rep. of Germany ......................... 128/303.17
855459  11/1960  United Kingdom ........... 128/303.17

Primary Examiner—Lee S. Cohen
Attorney, Agent, or Firm—Burns, Doane, Swecker & Mathis

[57] ABSTRACT

In the arrangement according to the invention for the high frequency coagulation of protein, in particular for surgical purposes, the protein impedance is continuously determined during application of high frequency power and the differential quotient for the impedance curve is formed according to time. The values of the differential quotient serve on the one hand for adjusting the initial power and on the other hand for establishing the optimal time for switching off the high frequency power. For both situations, provision is made for presettings making the arrangement according to the invention flexible and simple to adapt. The arrangement is preferably intended for bipolar coagulation instruments but use with unipolar instruments is also possible.

15 Claims, 3 Drawing Figures

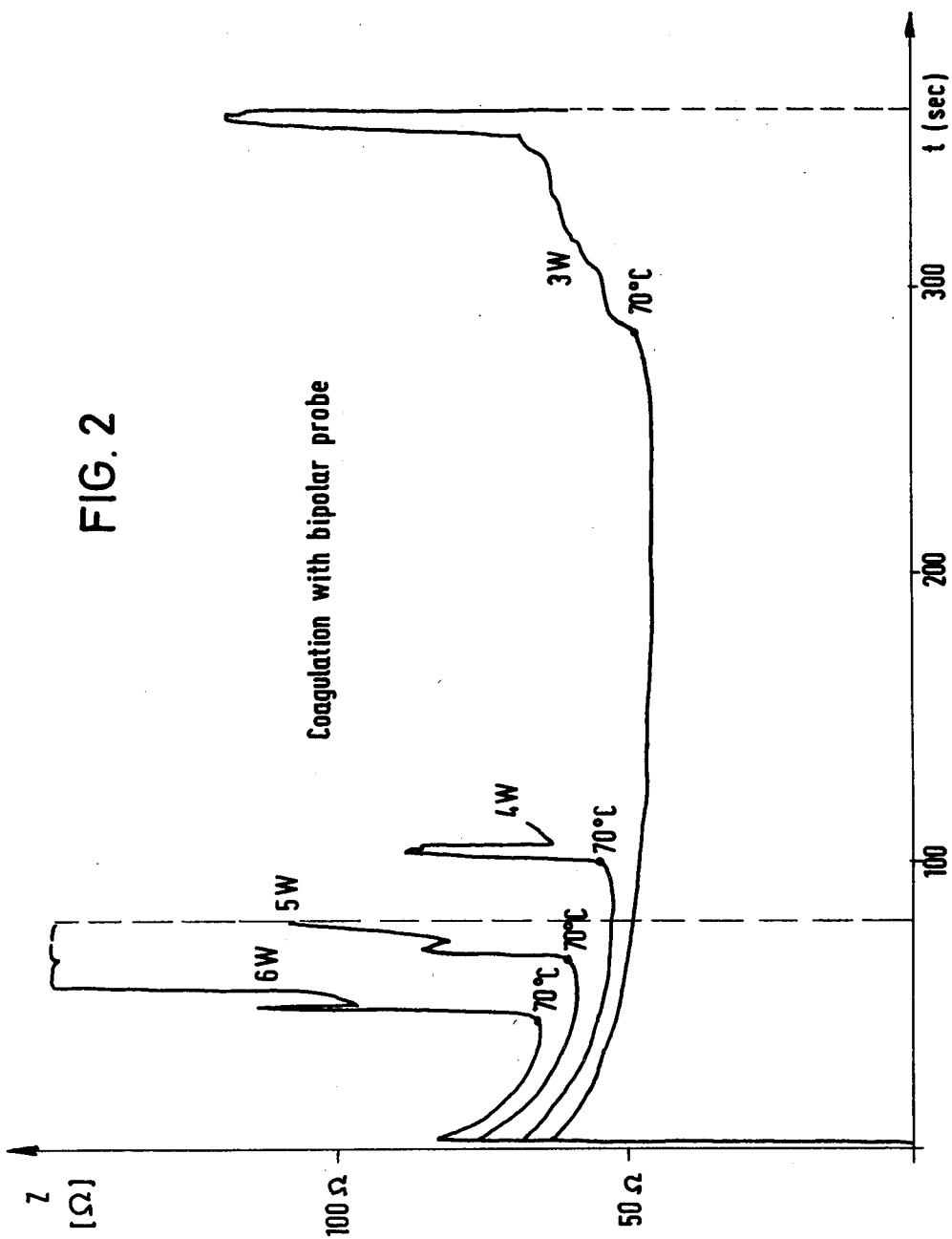

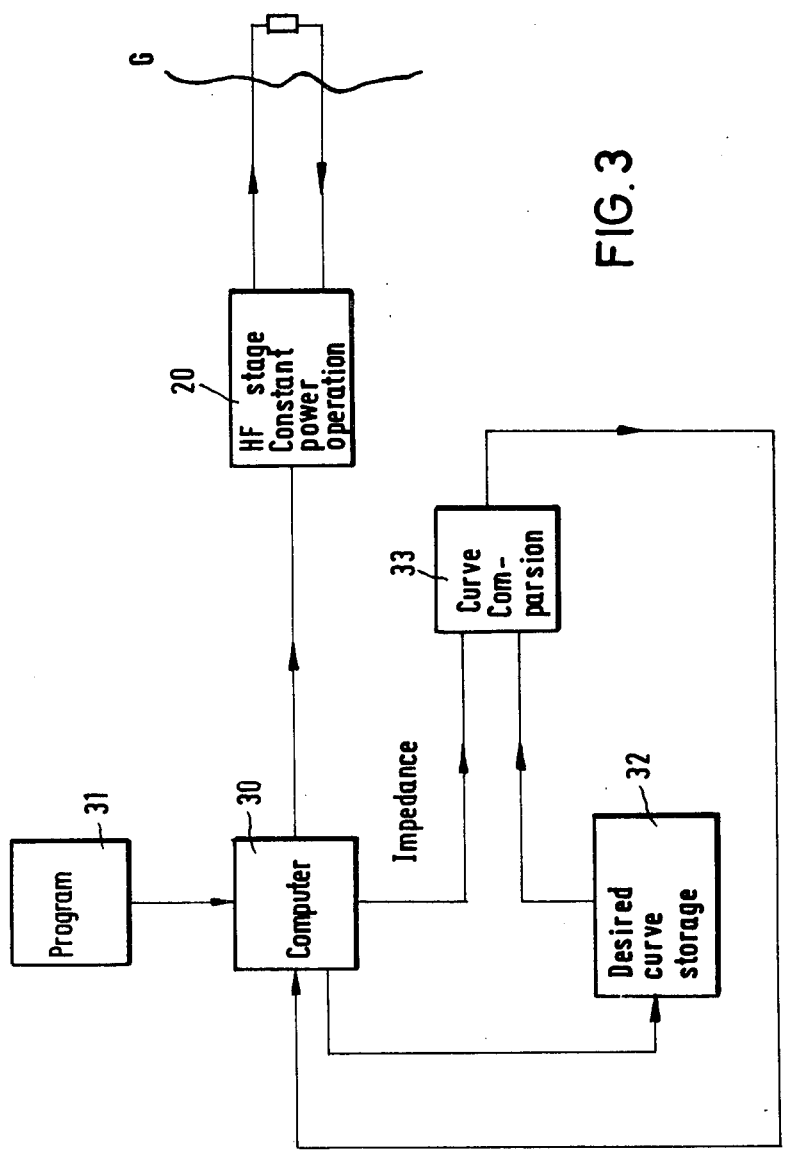

METHOD AND APPARATUS FOR THE HIGH FREQUENCY COAGULATION OF PROTEIN FOR SURGICAL PURPOSES

The invention relates to an arrangement for the high frequency coagulation of protein for surgical purposes, comprising a means for measuring the protein impedance and a coagulation instrument.

With the coagulation devices known hitherto, it is not possible to automatically achieve a determinate coagulate in different body tissue and with different instruments. It is known that a thermoelement be incorporated into the coagulation instrument. However, conditioned by the dimensions of the sensor and by the wiring, limits are set to such incorporation of thermoelements in instruments. Even with the most complicated of sensors, it is always only the sensor temperature and not the critical tissue temperature which can be determined.

Medical science demands a controllable and close localization of the coagulation focus, which is to remain limited to the desired area in order that no damage is sustained by important structures in the immediate vicinity. It is important that the coagulation be limited only to denaturation of the tissue and that no charring with scabbing take place at the tips of the instrument.

The reprint in "Zentralblatt für Chirurgie", Vol. 85, 1960 No. 19, p. 1052 to 1063, has disclosed working without a thermoelement. In the known arrangement, use is also made of recording of the resistance to monitor the coagulation. If the resistance is made directly measurable and is recorded while the coagulation is in course, without any delay in time, it is possible to immediately detect the beginning of the rise in resistance and to reduce the current and the temperature by hand or by corresponding automatic feedback. Thus, scabbing and blistering with ensuing rupture of the coagulate is avoided. The said publication does not pay regard to the fact that especial importance is to be attached to the high frequency power set at the beginning of the coagulation. If the power is too low, no coagulation takes place. If the power is preselected to be too high, then this gives rise to tissue burns. Furthermore the initial power to be set is dependent on the volume of the desired coagulation focus and the differing conductivity of the tissue. This inhomogeneity of the tissue to be coagulated and the varying electrode surfaces, particularly when the electrodes and their spacing is small, make it difficult for the operating surgeon to decide on what power range is to be preselected before the start of coagulation. Even if the power is initially set to a low value, during its subsequent increase it is not possible to set the optimum power by hand due to thermal time constants and dynamic events taking place. Furthermore, the tests described in the reprint show that the resistance curve takes an extremely flat course, so that it is extremely difficult to determine when coagulation has taken place to the desired extent. As mentioned above, an optimal result is not achieved by subsequently regulating the current down, as is proposed in the paper.

An object underlying the invention is to develop an arrangement for the high frequency coagulation of protein in such a way that the power output is automatically controlled in an optimal manner from the beginning of the coagulation operation and, after the desired coagulation volume has been formed, is switched off in a dependable manner without any extra check on the part of the operating surgeon.

This object is accomplished according to the invention in that the protein impedance is continuously measured and the differential quotient of said impedance is formed and is used to control the high frequency power employed.

In the invention it was discovered that the differential quotient of the protein impedance curve is an important indication not only for the final formation of the coagulate but also for the initial setting. It is therefore precisely in the initial state that uncontrolled occurences in the coagulation are avoided. It has furthermore proved that continuous coagulation shortly before the zero value of the differential quotient is reached leads to optimal, homogenous coagulation zones without burns. With the arrangement according to the invention, the desired size of the coagulate can be achieved in a simple way by presetting the differential quotient to a desired value which determines time and power value.

The invention is based on the finding that, regardless of the respective tissue structure, with bipolar coagulation instruments and with the use of different power values over different periods of time, there is given rise to protein impedance curves which in each case take the same characteristic course. The differential quotient of the protein impedance is of especial significance for the initial regulation of the high frequency power and for the attainment of optimal coagulation.

Embodiments of the invention are described below with the help of drawings in which FIG. 1 is a block diagram of an analog embodiment of the arrangement according to the invention, FIG. 2 is a diagram illustrating the course of typical protein or tissue impedance curves for different power and time, and FIG. 3 is a block diagram of a digital embodiment of the arrangement according to the invention.

The block diagram illustrated in FIG. 1 indicates a tissue G into which a coagulation instrument is introduced. The values of the tissue impedance Z are continuously established by means of an impedance measuring means 10 and are differentiated in a differentiator 11. The output signal of the differentiator 11 is hence a measure for the differential quotient of the tissue impedance curve. This signal is supplied to an I-controller 12, the output of which is connected to an analog storage 14 through an analog switch 13. The I-controller 12 is furthermore supplied with a voltage which can be set through a potentiometer P1 and corresponds to a certain preset value of the differential quotient. This voltage is also supplied to a first comparator V1 which compares it with the output signals of the differentiator 11, i.e. with the differential quotient of the tissue impedance curve. This arrangement serves for the high frequency power to be optimally set at the beginning of the coagulation operation, depending on the desired volume of coagulation, whereby the power and the duration of its use are correlated with one another, as may be seen from the diagram in FIG. 2. By means of the potentiometer P1, the rate of coagulation, i.e. the volume per unit of time, can be preselected.

A monitor 17 is also connected to the differentiator 11 and provides acoustic and/or optical indication on the course of the differential quotient. In particular, upon variation of the differential quotient, the pitch of tone can likewise vary in the same direction. The monitor 17 can be adapted to be preset from the impedance measuring means 10 for various orders of magnitude of the impedance.

A second comparator V2 receives a voltage set through a potentiometer P2 and likewise compares this voltage with the output values of the differentiator 11. The potentiometer P2 is set to a value of the differential quotient which is near zero. In particular, shortly before the minimum of the impedance time curve (differential quotient =zero), the value of the differential quotient of the differentiator 11 sinks to said value near zero. Then the comparator V2 determines conformity and switches off a high frequency final stage 20, for instance through a relay with contact r.

The way in which the arrangement according to FIG. 1 operates is as follows. When the switch S closes, the high frequency final stage 20 is switched on and power is gradually built up through the control circuit of elements 10,11,12,13 and 14. The impedance value is delivered as a continuous signal by the impedance measuring means 10 to the differentiator 11 which in turn applies a continuous signal to the I-controller 12. After the switching on, the I-controller 12 delivers an output voltage rising linearly from zero as long as the voltage difference between the voltage from the potentiometer P1 and the voltage which is at the output of the I-controller 12 and corresponds to the present differential quotient is not equal to zero. The output voltage of the I-controller 12 is applied through the analog switch 13 to the analog storage 14 which, by way of example, may take the form of sample and hold circuit. The output of the high frequency final stage 20 is then increased according to the value delivered by the analog storage. If the value of the differential quotient reaches the value set by the potentiometer P1, then the comparator V1 opens the analog switch 13, so that the high frequency final stage 20 is operated with constant power in accordance with the value stored in the analog storage 14.

The heating of the tissue now progresses, the impedance gradually reducing as shown by the curves in FIG. 2. The value of the differential quotient runs from a negative initial value towards zero in accordance with the progression of coagulation. When the value set through the potentiometer P2 is reached, the comparator V2 switches off the high frequency final stage 20, because then the desired coagulation is concluded. Otherwise, depending on the position of the working point on the power-load resistance characteristic curve of the coagulate, the power might rise steeply directly after the zero value of the differential quotient, which could lead to tissue burns and scabbing.

The diagram in FIG. 2 illustrates curves with different power values between 3 and 6 watts, the coagulate sizes being the same in each case. It is of interest to note the different negative gradient in the initial part of the curves with different HF power. This value can be used for automatically setting the coagulation power at the start of the coagulation. If the power is set in such a way through the potentiometer P1, the desired coagulate is always obtained in the same time, even under different conditions.

It is hence apparent that at the beginning of the entire operation, a controlled and regulated setting of the power can be achieved by the potentiometer P1.

With the help of FIG. 1, an analog embodiment of the arrangement according to the invention was described. However, the arrangement according to the invention can also be designed for a digital mode of operation. In this case, the measured impedance values are digitalized with a high, sampling frequency. The differential quotient can then be determined by a computer which passes the corresponding values on to the elements as are indicated in FIG. 1, these being of analog or digital design.

FIG. 3 illustrates the use of a computer in the arrangement of digital design according to the invention. A computer 30 is controlled by way of a program 31 which, depending on the desired parameters, in accordance with the settings of potentiometers P1 and P2, initiates the various program steps in the computer. The continuously measured impedance values are digitalized and supplied to the computer. The computer has a desired curve storage 32 storing various impedance curves and the values of the differential quotient of these impedance curves according to time. As indicated at 33, curve comparison then takes place with comparison of the differential quotients of the measured impedance curve and the selected desired curve. The value derived therefrom is supplied to the computer 30 which then applies a signal corresponding to the output signal of the analog storage 13 to the high frequency final stage 20. As in the analog embodiment according to FIG. 1, the control is such that the high frequency power is kept as constant as possible.

What is claimed is:

1. A method for coagulating protein tissue, comprising the steps of:
    applying a high-frequency signal to the tissue to be coagulated;
    measuring the impedance of the tissue, to which the high-frequency signal is applied;
    determining the differential quotient of the measured impedance by detecting the change of impedance over time; and
    controlling at least one of the power and duration of said high-frequency signal in accordance with said differential quotient.

2. The method of claim 1 wherein the application of said high-frequency signal to the tissue is terminated in response to said differential quotient reaching a predetermined value.

3. The method of claim 2 further including the step of terminating the application of said high-frequency signal to the tissue when said differential quotient is at a value near zero.

4. The method of claim 3 wherein said application is terminated shortly before said differential quotient reaches the zero value.

5. The method of claim 1 wherein the power level of said high-frequency signal is determined in response to said differential quotient reaching a preselected value, and the length of time during which the signal is applied to the tissue is determined in response to said differential quotient reaching a preselected value.

6. Apparatus for coagulating protein tissue, comprising:
    means for generating a high-frequency signal;
    means for applying said high-frequency signal to the tissue to be coagulated;
    means for measuring the impedance of the tissue to which the high-frequency signal is applied;
    means for detecting the change of the measured impedance over time to thereby determine the differential quotient of the measured impedance; and
    means for controlling said high-frequency generating means in response to the determined differential quotient.

7. The apparatus of claim 6, wherein said differential quotient determining means comprises a differentiator, and said controlling means comprises a current controller and means for storing an output signal produced by said current controller and applying the stored signal to said high-frequency generating means.

8. The apparatus of claim 7 further including a comparator for comparing said differential quotient with a preselected value and means responsive to said comparator for interrupting further storage of the output signal of said current controller when said differential quotient reaches said preselected value.

9. The apparatus of claim 8 wherein said interrupting means comprises a switch for selectively applying the output signal of said current controller to said storage means.

10. The apparatus of claim 8 further including means for indicating when said differential quotient reaches said preselected value.

11. The apparatus of claim 6, wherein said controlling means includes a comparator for comparing said differential quotient with a preselected value and means responsive to said comparator for interrupting the high-frequency signal applied to the tissue when said differential quotient reaches said preselected value.

12. The apparatus of claim 11 further including means for indicating when said differential quotient reaches said preselected value.

13. The apparatus of claim 6 wehrein said differential quotient determining means and said controlling means are implemented in a digital computer system having stored therein the values of various impedance curves and their differential quotients for different power/time parameters and which produces an output control signal to said high frequency generating means as a function of the comparison of the actual determined values of the differential quotient with said stored values.

14. The apparatus of claim 6 wherein said signal applying means comprises a bipolar coagulation instrument.

15. The apparatus of claim 6 wherein said signal applying means comprises a unipolar coagulation instrument.

* * * * *